United States Patent [19]
Jouquey et al.

[11] 4,152,325
[45] May 1, 1979

[54] NOVEL STEROIDS AND THEIR USE

[75] Inventors: Alain Jouquey, Paris; André Pierdet, Noisly-le-Sec, both of France

[73] Assignee: Roussel Uclaf, Paris, France

[21] Appl. No.: 855,177

[22] Filed: Nov. 28, 1977

[30] Foreign Application Priority Data
Dec. 14, 1976 [FR] France .................. 76 37623

[51] Int. Cl.² .......................................... C07J 71/00
[52] U.S. Cl. ........................ 260/239.55 R; 260/397.4; 260/397.5
[58] Field of Search ........ 260/239.55, 397.4, 397.5 A, 260/239.55 R, 397.5

[56] References Cited
U.S. PATENT DOCUMENTS
3,257,391  6/1966  Bowers et al. ................. 260/239.55

FOREIGN PATENT DOCUMENTS
853012  11/1960  United Kingdom ................. 260/397.4

Primary Examiner—Elbert L. Roberts
Attorney, Agent, or Firm—Hammond & Littell

[57] ABSTRACT

Novel pregnatetraenes of the formula

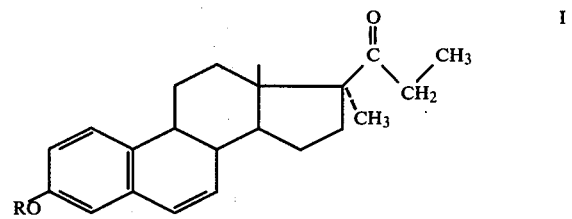

wherein R is selected from the group consisting of hydrogen, alkyl of 1 to 4 carbon atoms, tetrahydropyranyl, trityl and trimethylsilyl and intermediates therefore and a process for their preparation and a process for the preparation of tritium labelled steroids.

10 Claims, No Drawings

NOVEL STEROIDS AND THEIR USE

STATE OF THE ART

The use of 17α,21-dimethyl-[6,7-$^3$H]-19-nor-Δ$^{4,9}$-pregnadiene-3,20-dione for the characterization of progesterone reception is described in numerous publications such as Raynaud et al. [Steroids, July 1973, p. 89–97] and the said product has a specific activity on the order of 50 Ci/mM. The said product permits the dosage of specific receptor of progesterone in uterine cytosol or in the cycloplasma of tumor cells (cancer) and in induced tumors provoked by DMBA (9,10-dimethyl-1,2-benzanthracene) in the rat. The product has the advantage compared to progesterone as it is not fixed by transcortine and has an affinity for the reception of progesterone 6 to 8 times greater than the affiity for the latter.

OBJECTS OF THE INVENTION

It is an object of the invention to provide the novel compounds of formula I and to a novel process for their preparation and novel intermediates therefore.

It is another object of the invention to provide a novel process for the preparation of tritium labelled steroids and novel intermediates produced therein.

These and other objects and advantages of the invention will become obvious from the following detailed description.

THE INVENTION

The novel compounds of the invention are pregnatetraenes of the formula

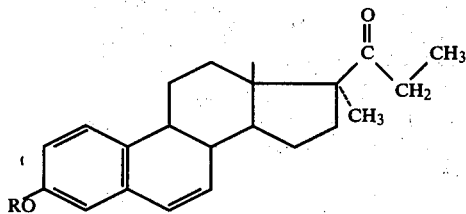

I wherein R is selected from the group consisting of hydrogen, alkyl of 1 to 4 carbon atoms, tetrahydropyranyl, trityl and trimethylsilyl.

Examples of R when it is alkyl are methyl, ethyl, propyl, isopropyl, butyl, sec-butyl or tert.-butyl. Specific compounds of formula I are 17α, 21-dimethyl-19-nor-Δ$^{1,3,5(10),6}$-pregnatetraene-3-ol-20-one, 3-methoxy-17α, 21-dimethyl-19-nor-Δ$^{1,3,5(10),6}$-pregnatetraene-20-one and 6-(αtetrahydropyranyloxy)-17α, 21-dimethyl-19-nor-Δ$^{1,3,5(10),6}$-pregnatetraene-20-one.

The novel process for the preparation of the steroids of the formula I comprises reacting Δ$^{1,3,5(10),6}$-estratetraene-3-ol-17-one with an ethynylation agent to form 17α-ethynyl-Δ$^{1,3,5(10),6}$-estratetraene-3,17β-diol, reacting the latter with an organic carboxylic acid or a functional derivative thereof to form 3,17β-diacyloxy-17α-ethynyl-Δ$^{1,3,5(10),6}$-estratetraene, reacting the latter with a hydration agent to form 3,17β-diacyloxy-17α-acetyl-Δ$^{1,3,5(10),6}$-estratetraene, reacting the latter with an alkali metal in ammonia and methyl halide to simultaneously methylate in the 17-position and isomerize the 17-acetyl group to form 3-acyloxy-17α-methyl-19-nor-Δ$^{1,3,5(10),6}$-pregnatetraene-20-one, saponifying the latter with a strong aqueous base to form 17α-methyl-19-nor-Δ$^{1,3,5(10),6}$-pregnatetraene-3-ol-20-one, blocking the 3-hydroxy group of the latter with dihydropyran, trityl chloride, trimethylsilyl chloride or an alkyl generating agent to obtain 3-OR'-17α-methyl-19-nor-Δ$^{1,3,5(10),6}$-pregnatetraene-20-one when R' is R other than hydrogen, reacting the latter with a methyl halide in the presence of a catalyst to obtain 3-OR'-17α, 21-dimethyl-19-nor-Δ$^{1,3,5(10),6}$-pregnatetraene-20-one (formula I where R is other than hydrogen) which may be optionally treated with an acid to obtain 17α, 21-dimethyl-19-nor-Δ$^{1,3,5(10),6}$-pregnatetraene-3-ol-20-one (formula I where R is hydrogen) which is optionally etherified in the 3-position.

In a preferred mode of the process of the invention, the ethynylation agent is potassium acetylide and the reaction is effected in tetrahydrofuran in the presence of potassium tert.-butylate. The esterification of the 3 and 17-OH groups is effected with acetic anhydride in the presence of p-toluence sulfonic acid although othercarboxylic acids of 1 to 18 carbon atoms such as formic acid, propionic acid, butyric acid, isobutyric acid, undecylic acid, cyclopentylacetic acid, cyclohexylacetic acid, cyclopentylpropionic acid, cclohexylpropionic acid, phenylacetic acisd, phenylpropiionic acid, p-nitrobenzoic acid or trifluoroacetic acid may be used.

The preferred hydration agent is Dowex 50 resin activated by mecuric acetate and the reaction is effected in ethanol. The methylation and simulatenous isomerization is effected with lithium in ammonia and methyl iodide effected in tetrahydrofuran with cooling and the saponification of the 3-acyloxy group is effected with sodium hydroxide in ethanol. The blocking of the 3-hydroxy is preferably effected with dihydropyran in tetrahydrofuran in the presence of p-toluene sulfonic acid and the 21-methylation is effected with methyl iodide in toluence in the presence of potassium tert.-butylate. The preferred acid to free the 3-hydroxy group is preferably aqueous acetic acid or a hydro acid such as hydrochloric acid. The alkyl generating compound to etherify the 3-hydroxy group is preferably dimethylsulfate in acetone in the presence of sodium hydroxide.

The novel intermediates of the invention are 17α-ethynyl-Δ$^{1,3,5(10),6}$-estratetraene-3,17β-diol, 3,17β-diacetoxy-17α-ethynyl-Δ$^{1,3,5(10),6}$-estratetraene, 3,17β-diacetoxy-17α-acetyl-Δ$^{1,3,5(10),6}$estratetraene, 3-acetoxy-17α-methyl-19-nor-Δ -Δ$^{1,3,5(10),6}$-pregnatetraene-20-one, 17α-methyl-19-nor-Δ$^{1,3,5(10),6}$-pregnatetraene-3-ol-20-one and 3-(α-tetrahyropyranyloxy)-17α-methyl-19-nor-Δ$^{1,3,5(10),6}$,pregnatetraene-20-one.

The products of formula I are useful for the preparation of steroids labelled with a tritium atom. the novel process of the invention forthe preparation of labelled steroids comprises reacting a compound of formula I wherein R is other than hydrogen with tritium hydrogen in the presence of a catalyst to obtain 3-OR-17α, 21-dimethyl-[6,7-$^3$H]-19-nor-Δ$^{1,3,5(10)}$-pregnatriene-20-one and when R is methyl, subjecting the latter to the Birch reaction with lithium in ammonia to obtain 3-methoxy-17α, 21-dimethyl-[6,7$^3$H]-19-nor-Δ$^{2,5(10)}$-pregnadiene-20-ξ-ol or when R is a group other than methyl, reacting the said compound with an acid to form 17α, 21-dimethyl[6,7-$^3$H]-19-nor-Δ$^{1,3,5(10)}$-pregnatriane-3-ol-20-one, reacting the latter with dimethylsulfate to obtain 3-methoxy-17α,21-dimethyl-[6,7-$^3$H]-19-non-Δ$^{1,3,5(10)}$-pregnatriene-20-one and reacting the latter with lithium in ammonia in the Birch reaction to form 3-methoxy-17α, 21-dimethyl-[6,7-$^3$H]-Δ$^{2,5(10)}$- pregnadiene-20-ξ-ol, reacting the latter with a weak aqueous acid such as acetic acid to form 17α, 21-dimethyl-[6,7-$^3$H]-19-nor-Δ$^{5(10)}$-pregnene-20-ξ-ol-3-one, subjecting the latter to reaction with pyradium perbromide to form 17α, 21-dimethyl-[6,7-$^3$H]-19-nor-Δ$^{4,9}$-pregnadiene-20-ξ-ol-3-one and reacting the latter with aqueous sulfochromic acid solution to form 17α, 21-dimethyl-[6,7-$^3$H]-19-nor-Δ$^{4,9}$-pregnadiene-3, 20-dione.

The novel intermediates prepared in the latter are 3-methoxy-17α, 21-dimethyl-[6,7-$^3$H]-19-nor-Δ$^{1,3,5(10)}$-pregnatriene-20-one, 17α, 21-dimethyl-[6,7-$^3$H]-19-nor-Δ$^{5(10)}$-pregnene-20-ξ-ol-3-one, 17α, 21-dimethyl-[6,7-$^3$H]-19-nor-Δ$^{4,9}$-pregnadiene-20-ξ-ol-3-one and especially 3-methoxy-17α, 21-dimethyl-[6,7-$^3$H]-19-nor-Δ$^{2,5(10)}$-pregnadiene-20-ξ-ol.

The starting material for the preparation of the compounds of formula I, namely Δ$^{1,3,5(10),6}$-estratetraene-3-ol-17-one, is described in U.S. Pat. No. 2,280,828.

In the following examples there are described several preferred embodiments to illustrate the invention. However, it should be understood that the invention is not intended to be limited to the specific embodiments.

EXAMPLE 1

3-methoxy-17α, 21-dimethyl-19-nor-Δ$^{1,3,5(10),6}$-pregnatetraene-20-one

STEP A:
17α-ethynyl-Δ$^{1,3,5(10),6}$-estratetraene-3,17β-diol

Acetylene was bubbled into 470 ml of tetrahydrofuran cooled to about 2° C. and then 23.5 g of potassium tert.-butylate followed by 43 ml of hexamethylphosphorotriamide were added thereto. The mixture was stirred at 2° C. for 40 minutes and a solution of 11.75 g of Δ$^{1,3,5(10),6}$-estratetraene-3-ol-17-one in 350 ml of tetrahydrofuran was added thereto. The mixture was stirred for 2 hours at 2° C. while bubbling acetylene therethrough and then 500 ml of water were added. The pH of the mixture was adjusted to 5–6 with acetic acid and the organic phase was decanted. The aqueous phase was extracted with ether and the ether extracts were washed with water, dried, treated with activated carbon, vacuum filtered and evaporated to dryness under reduced pressure to obtain 13.9 g of 17α-ethynyl-Δ$^{1,3,5(10),6}$-estratetraene-3,17β-diol which was used as is for the next step. A sample crystallized from methylene chloride melted at 178° C.

STEP B:
3,17β-diacetoxy-17α-ethynyl-Δ$^{1,3,5(10),6}$-estratetraene

A mixture of 13.9 g of the product of Step A, 1.04 g of p-toluene sulfonic acid and 33 ml of acetic acid anhydride was stirred at room temperature for 2½ hours and was vacuum filtered. The recovered precipitate was washed with acetic acid and then with water until the wash waters were neutral and dried to obtain 11.1 g of 3,17β-diacetoxy-17α-ethynyl-Δ$^{1,3,5(10),6}$-estratetraene melting at 189°–190° C.

STEP C:
3,17β-diacetoxy-17α-acetyl-Δ$^{1,3,5(10),6}$-estratetraene 22 g of Dowex 50 resin (a strongly acid ion exchange resin) activated with mercuric acetate were added to a suspension of 11.05 g of the product of Step B in 165 ml of ethanol and the mixture was refluxed for 16 hours. The mixture was filtered while hot and the filter was rinsed with ethanol. The filtrate was evaporated to dryness and the residue was added to 44 ml of anhydrous pyridine and 22 ml of acetic acid anhydride. The mixture was stirred at room temperature for 2 hours and was then added to a ice-water mixture. The crystallized product was recovered by vacuum filtration, was washed with water and dried in an oven at 80° C. to obtain 10.92 g of 3,17β-diacetoxy-17β-diacetoxy-17α-acetyl-Δ$^{1,3,5(10),6}$-estratetraene melting at 196° C.

STEP D:
3-acetoxy-17α-methyl-19-nor-Δ$^{1,3,5(10),6}$-pregnatetraene-20-one

A mixture of 150 ml of ammonia and 570 mg of lithium stood at −70° C. for 15 minutes and then 150 ml of tetrahydrofuran cooled to −68° C. were added thereto. 10.88 g of the product of Step C were added thereto and the mixture was stirred under an inert atmosphere for 105 minutes. 44 ml of methyl iodide were added thereto over 10 minutes and the mixture was held at −69° C. for 90 minutes after which the temperature rose to 15°–20° C. The reaction mixture was washed with water and the aqueous phase was extracted with ether. The ether phase was washed with water until the wash waters were neutral, was dried and evaporated to dryness. The residue was chromatographed over silica gel and was eluted with a 1–9 ethyl acetate-benzene mixture to obtain a fraction from which 3.22 g of product crystallized. 13 ml of pyridine and 6.5 ml of acetic acid anhydride were added to the fraction and the mixture was stirred for 90 minutes in a closed vessel. Ice was added thereto and the mixture was diluted with water and was vacuum filtered. The recovered product was washed with water, dried and chromatographed over silica gel. Elution with a 2–8 ether-petroleum ether (b.p. = 60°–80° C.) mixture yielded 1.71 g of 3-acetoxy-17α-methyl-19-nor-Δ-$^{1,3,5(10),6}$-pregnatetraene-20-one melting at 140°–142° C.

STEP E:
17α-methyl-19-nor-Δ$^{1,3,5(10),6}$-pregnatetraene-3-ol-20-one

A suspension of 1.03 g of the product of Step D, 20 ml of absolute ethanol and 2.9 ml of N sodium hydroxide was stirred at 20° C. under an inert atmosphere for one hour and the pH of the mixture was adjusted to 5–6 with acetic acid addition. The mixture was diluted with water and was vacuum filtered. The recovered product was washed with water and dried to obtain 805 mg of 17α-methyl-19-nor-Δ$^{1,3,5(10),6}$-pregnatetraene-3-ol-20-one melting at 252° C.

STEP F:
3-(α-tetrahydropyranyloxy)-17α-methyl-19-nor-Δ$^{1,3,5(10),6}$-pregnatetraene-20-one A mixture of 0.8 g of the product of Step E, 16 ml of tetrahydrofuran, 0.8 ml of dihydropyran and 16 mg of p-toluene sulfonic acid was stirred under an inert atmosphere at 20° C. for 90 minutes and after the addition of 0.4 ml of dihydropyran thereto, the mixture was held at 20° C. for 4 hours. Then, 10 ml of a saturated sodium bicarbonate solution were added thereto and the mixture was extracted with ethyl acetate. The organic extracts were washed with water, dried and evaporated to dryness and the residue was chromatographed over silica gel. Elution with a 9–1 benzene-ethyl acetate mixture yielded 1 g of 3-(α-tetrahydropyranyloxy)-17α-methyl-19-nor-Δ$^{1,3,5(10),6}$-pregnatetraene-20-one melting at ~124° C.

STEP G:
3-(α-tetrahydropyranyloxy)-17α,21-dimethyl-19-nor-Δ$^{1,3,5(10),6}$-pregnatetraene-20-one 420 mg of potassium tert.-butylate were added to a solution of 740 mg of the product of Step F in 7.5 ml of toluene under an inert atmosphere and the mixture was stirred at 20° C. for 15 minutes. 0.475 ml of methyl iodide were added to the mixture which was then left overnight at room temperature and the mixture was poured into water. The mixture was extracted with ethyl acetate and the organic extracts were washed with water until the wash waters were neutral, dried and evaporated to dryness under reduced pressure. The residue was chromatographed over silica gel and was eluted with a 9-1 benzene-ethyl acetate mixture to obtain one fraction of 495 mg of product and a second fraction of 210 mg of final product and starting material. Treatment of the second fraction resulted in a total yield of 612 mg of 3-(α-tetrahydropyranyloxy)-17α,21-dimethyl-19-nor-Δ$^{1,3,5(10),6}$-pregnatetraene-20-one in the form of a resin with an Rf = 0.45.

STEP H:
17α,21-dimethyl-19-norΔ$^{1,3,5(10),6}$-pregnatetraene-3-ol-20-one

A solution of 0.57 g of the product of Step G in 5.8 ml of acetic acid containing 20% of water was stirred at 50° C. for one hour and the reaction mixture was then poured into water. The mixture was extracted with methylene chloride and the organic extracts were washed with water, dried and evaporated to dryness under reduced pressure. The residue was twice chromatographed over silica gel and was eluted with a 9-1 benzene-ethyl acetate mixture and then petroleum ether (b.p. = 60°-80° C.) to obtain 73 mg of 17α,21-dimethyl-19-nor-Δ$^{1,3,5(10),6}$-pregnatetraene-3-ol-20-one melting at 209° C.

Analysis: $C_{22}H_{28}O_2$: Calculated: %C, 81.45; %H, 8.70. Found: %C, 80.9; %H, 8.7.

STEP I:
3-methoxy-17α,21-dimethyl-19-nor-Δ$^{1,3,5(10),6}$-*pregnatetraene*-20one A mixture of 50 mg of the product of step H, 5 ml of acetone and 3 ml of 2N sodium hydroxide solution was refluxed. 0.5 ml of dimethyl sulfate and 2 ml of 2N sodium hydroxide solution were added thereto and the mixture was allowed to stand for 10 minutes. Then, another 0.5 ml of dimethyl sulfate and 2 ml of 2N sodium hydroxide solution were added to the reaction mixtures which was stirred for 10 minutes and was then poured into 10 ml of water. The mixture was extracted with benzene and the organic extracts were washed with water, dried and evaporated to dryness to obtain 57 mg of 3-methoxy-17α,21-dimethyl-19-nor-Δ$^{1,3,5(10),6}$-pregnatetraene-20-one in the form of crystals with an Rf = 0.7 (silica chromatography — 7-3 benzene-ethyl acetate mixture).

EXAMPLE 2
17α,21-dimethyl-[6,7-$^3$H]-19-nor-Δ$^{4,9}$-pregnadiene-3,20-dione

STEP A:
3-methoxy-17α,21-dimethyl-[6,7-$^3$H]-19-nor-Δ$^{1,3,5(10)}$-pregnatriene-20-one A mixture of 10 mg of palladized carbon black, 57 mg of 3-methoxy-17α,21-dimethyl-19-nor-Δ$^{1,3,5(10),6}$-pregnatetraene-20-one and 1.5 ml of ethyl acetate was cooled in liquid ammonia and then 3.86 ml of tritium at normal pressure at 0° C. and with a specific activity of 2590 mCi/ml were added under reduced pressure. The mixture was allowed to return to room temperature and was then stirred for 3 hours. Excess tritium was recovered and the mixture was filtered. The filtrate was evaporated to dryness under reduced pressure and after elimination of labile tritium, there were recovered 44 mg of 3-methoxy-17α,21-dimethyl-19-nor-Δ$^{1,3,5(10)}$-pregnatriene-20-one with a specific activity of 51 Ci/m-mole.

STEP B:
3-methoxy-17α,21-dimethyl-[6,7-$^3$H]-19nor-Δ$^{2,5(10)}$-pregnadiene-20-ξ-ol 0.5 ml of ethanol and 200 mg of lithium were added to 25 ml of ammonia cooled to −35 to −40° C. and 44 mg of the product of Step A in 5 ml of tetrahydrofuran and the mixture was stirred for one hour at −35° C. 10 ml ethanol were added to the mixture over 10 minutes and the ammonia was removed at room temperature. The mixture was extracted with methylene chloride and the extracts were dried over sodium sulfate and evaporated under reduced pressure to dryness to obtain 48 mg of 3-methoxy-17α,21-dimethyl-[6,7-$^3$H]-19-nor-Δ$^{2,5(10)}$-pregnadiene-20-ξ-ol in the form of a resin which was used as is for the next step.

STEP C:
17α,21-dimethyl-[6,7-$^3$H]-19-nor-Δ$^{5(10)}$-pregnene-20-ξ-ol-3-one A mixture of 48 mg of the product of Step B in 2 ml of acetic acid containing 25% of water was stirred under an inert atmosphere for 5 hours and then water was added thereto. The mixture was vacuum filtered and the recovered product was washed successively with water, a saturated sodium bicarbonate solution and then with water, was dried under reduced pressure. The residue was crystallized from methylene chloride-isopropyl ether to obtain 50 mg of 17α,21-dimethyl-[6,7-$^3$H]-19-nor-Δ$^{5(10)}$-pregnene-20-ξ-ol-3-one.

STEP D:
17α,21-dimethyl-[6,7-$^3$H]-19-nor-Δ$^{4,9}$-pregnadiene-20-ξ-ol-3-one A mixture of 50 mg of the product of Step C in 0.5 ml of pyridine was stirred at room temperature and after cooling the mixture to −14° C., 35 mg of pyridium perbromide were added thereto over 45 minutes. The mixture was held at −14° C. for 45 minutes and the temperature was allowed to return to 20° C. The mixture was stirred at 20° C. for 18 hours at room temperature under an inert atmosphere and was then poured into a mixture of 8-5-2 water-ice-hydrochloric acid. The mixture was stirred for 45 minutes and was vacuum filtered. The recovered product was washed with water until the wash waters were neutral and dried to obtain 52 mg of 17α,21-dimethyl-[6,7-$^3$H]-19-nor-Δ$^{4,9}$-pregnadiene-20-ξ-ol-3-one which was used as is for the next step.

STEP E:
17α,21-dimethyl-[6,7-$^3$H]-19-nor-Δ$^{4,9}$-pregnadiene-3,20-dione

A mixture of 52 mg of the product of Step D in 4 ml of acetone was stirred until complete dissolution occured and then 0.1 ml of a solutin of 5.1 g of chromic acid anhydride, 4.6 ml of sulfuric acid and 20 ml of water was added thereto at a temperature not below 25° C. The operation was repeated twice and the resulting mixture was added to water. The mixture was evaporated under reduced pressure at a temperature less than 35° C. and then cooled to 20° C. at reduced pressure. The mixture was vacuum filtered and the residue was washed with water until the wash waters were neutral. The 50 mg of product was chromatographed with plates and elution with an 85-15 benzene-ethyl acetate mixture to obtain 9 mg of 17α,21-dimethyl-[6,7-$^3$H]-19-norΔ$^{4,9}$-pregnadiene-3,20-dione with a specific activity of 51.4 Ci/mM.

Various modifications of the products and processes of the invention may be made without departing from the spirit or scope thereof and it is to be understood that the invention is intended to be limited only as defined in the appended claims.

We claim:

1. Pregnatetraenes of the formula

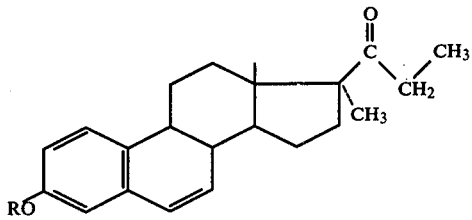

wherein R is selected from the group consisting of hydrogen, alkyl of 1 to 4 carbon atoms, tetrahydropyranyl, trityl and trimethylsilyl.

2. A compound of claim 1 which is 17α,21-dimethyl-19-nor-Δ$^{1,3,5(10),6}$-pregnatetraene-3-ol-20-one.

3. A compound of claim 1 which is 3-methoxy-17α,21-dimethyl-19-nor-Δ$^{1,3,5(10),6}$-pregnatetraene-20-one.

4. A compound of claim 1 which is 3-(α-tetrahydropyranyloxy)-17α,21-dimethyl-19-nor-Δ$^{1,3,5(10),6}$-pregnatetraene-20-one.

5. A process for the preparation of a compound of claim 1 comprising reacting Δ$^{1,3,5(10),6}$-estratetraene-3-ol-17-one with an alkali metal acetylide to form 17α-ethynyl-Δ$^{1,3,5(10),6}$-estratetraene-3,17β-diol, reacting the latter with an anhydride of an organic carboxylic acid of 1 to 18 carbon atoms to form 3,17β-diacyloxy-17α-ethynyl-Δ$^{1,3,5(10),6}$-estratetraene, reacting the latter with Dowex 50 resin activated with mercuric acetate to form 3, 17β-diacyloxy-17α-acetyl-Δ$^{1,3,5(10),6}$-estratetraene, reacting the latter with an alkali metal in ammonia and methyl halide to simultaneously methylate in the 17-position and isomerize the 17-acetyl group to form 3-acyloxy-17α-methyl-19-nor-Δ$^{1,3,5(10),6}$-pregnatetraene-20-one, saponifying the latter with a strong aqueous base to form 17α-methyl-19-nor-Δ$^{1,3,5(10),6}$-pregnatetraene-3-ol-20-one, blocking the 3hydroxy group of the latter with dihydropyran, trityl chloride, trimethylsilyl chloride or an alkyl generating agent to obtain 3-OR'-17α-methyl-19-nor-Δ$^{1,3,5(10),6}$-pregnatetraene-20-one when R' is R other than hydrogen, reacting the latter with a methyl halide in the presence of a catalyst to obtain 3-OR'-17α-,21-dimethyl-19-nor-Δ$^{1,3,5(10),6}$-pregnatetraene-20-one (claim 1 where R is other than hydrogen).

6. A compound selected from the group consisting of 17α-ethynyl-Δ$^{1,3,5(10),6}$-estratetraene-3,17β-diol, 3,17β-diacetoxy-17α-ethynyl-Δ$^{1,3,5(10),6}$-estratetranen, 3,17β-diacetoxy-17α-acetyl:Δ$^{1,3,5(10),6}$-estratetraene, 3-acetoxy-17α-methyl-19norΔ$^{1,3,5(10),6}$-pregnatetraene-20-one, 17α-methyl-19-nor-Δ$^{1,3,5(10),6}$-pregnatetraene-3-ol-20-one and 3-(α-tetra hydropyranyloxy)-17α-methyl-19-nor-Δ$^{1,3,5(10),6}$-pregnatetraene-20-one.

7. A process for the preparation of steroids labelled with a tritium atom comprising reacting a compound of claim 1 wherein R is other than hydrogen with tritium hydrogen in the presence of a catalyst to obtain 3-OR-17α,21-dimethyl-[6,7-$^3$H]-19-nor-Δ$^{1,3,5(10)}$-pregnatriene-20-one and when R is methyl, subjecting the latter to the Birch reaction with lithium in ammonia to obtain 3-methoxy-17α,21-dimethyl-[6,7-$^3$H]-19-nor-Δ$^{2,5(10)}$-pregnadiene-20-ξ-ol or when R is a group other than methyl, reacting the said compound with an acid to form 17α,21-dimethyl-[6,7-$^3$H]-19-nor-Δ$^{1,3,5(10)}$,-pregnatriene-3-ol-20-one, reacting the latter with dimethyl sulfate to obtain 3-methoxy-17α,21-dimethyl-[6,7-$^3$H]-19-nor-Δ$^{1,3,5(10)}$-pregnatriene-20-one and reacting the latter with lithium in ammonia in the Birch reaction to form 3-methoxy-17α,21-dimethyl-[6,7-$^3$H]-Δ$^{2,5(10)}$-pregnadiene-20-ξ-ol, reacting the latter with a weak aqueous acid to form 17α,2-dimethyl-[6,7-$^3$H]-19-nor-Δ$^{5(10)}$-pregnene-20-ξ-ol-3-one, subjecting the latter to reaction with pyridinium perbromide to form 17α,21-dimethyl-[6,7-$^3$H]-19-nor-Δ$^{4,9}$-pregnadiene-20-ξ-ol-3-one and reacting the latter with aqueous sulfochromic acid solution to form 17α,21-dimethyl-[6,17-$^3$H]-19-nor-Δ$^{4,9}$-pregnadiene-3,20-dione.

8. A compound selected from the group consisting of 3-methoxy-17α,21-dimethyl-[6,7-$^3$H]-19-nor-ξ$^{1,3,5(10)}$-pregnatriene-20-one, 17α,21-dimethyl-[6,7-$^3$H]-19-nor-pregnatriene-20-one, 17α,21-dimethyl-[6,7-$^3$H]-19-nor-Δ$^{5(10)}$-pregnene-20-ξ-ol-3-one, 17α, 21-dimethyl-[6,7-$^3$H]-19-nor-Δ$^{4,9}$-pregnadiene-20-ξ-ol-3-one and 3-methoxy-17α,21-dimethyl-[6,7-$^3$H]-19-nor-Δ$^{2,5(10)}$-pregnadiene-20-ξ-ol.

9. The process of claim 8 wherein the 3-OR'-17α,21-dimethyl-19-nor-Δ$^{1,35,(10),6}$-pregnatetraene-20-one is treated with an acid to obtain 17α, 21-dimethyl-19-nor-Δ$^{1,3,5(10),6}$-pregnatetraene3ol-20-one.

10. The process of claim 9 wherein the product is reacted with an etherification agent to obtain the corresponding compound of claim 1 wherein R is other than hydrogen.

* * * * *

UNITED STATES PATENT AND TRADEMARK OFFICE
CERTIFICATE OF CORRECTION

PATENT NO. : 4,152,325　　　　　　　　　　　　　　Page 1 of 2
DATED     : May 1, 1979
INVENTOR(S): ALAIN JOUQUEY and ANDRE PIERDET It is certified that error appears in the above-identified patent and that said Letters Patent are hereby corrected as shown below:

| Col. | Line | |
|---|---|---|
| 1 | 52 | "6-(αtetrahydro" should be --6-(α-tetrahydro-- |
| 2 | 18 | "othercar" should be --other-car-- |
| 2 | 23 | "phenylpropiionic" should be --phenylpropionic-- |
| 2 | 57 | delete one "Δ" |
| 2 | 52 | "the" should be --The-- |
| 2 | 53 | "forthe" should be --for the-- |
| 2 | 57 | "[6,7- $^3$H]" should be --[6,7-$^3$H]-- |
| 2 | 60 | "[6,7$^3$H]" should be --[6,7-$^3$H]-- |
| 3 | 14 | "[6,7$^3$H]" should be --[6,7-$^3$H]-19-- |

UNITED STATES PATENT AND TRADEMARK OFFICE
CERTIFICATE OF CORRECTION

PATENT NO. : 4,152,325
DATED : May 1, 1979
INVENTOR(S) : ALAIN JOUQUEY and ANDRE PIERDET It is certified that error appears in the above-identified patent and that said Letters Patent are hereby corrected as shown below:

| Col. | Line | | |
|---|---|---|---|
| 5 | 43 | "aene20one" should be --aene-20-one-- | |
| 8 | Claim 8 line 43 | "19-nor-$\zeta^{1,3,5(10)}$" should be --19-nor-$\Delta^{1,3,5(10)}$-- | |
| 8 | Claim 9 line 52 | "pregnatetraene3ol" should be --pregnatetrane-3-ol-- | |

Signed and Sealed this

Fifteenth Day of January 1980

[SEAL]

Attest:

SIDNEY A. DIAMOND

Attesting Officer    Commissioner of Patents and Trademarks